United States Patent [19]
Mrklas et al.

[11] Patent Number: 5,304,112
[45] Date of Patent: Apr. 19, 1994

[54] STRESS REDUCTION SYSTEM AND METHOD

[75] Inventors: Theresia A. Mrklas, 715 High St., Bedford, Ohio 44146; Maurice B. Daniel, Alexandria, Va.; William B. Daniel, Twinsburg, Ohio

[73] Assignee: Theresia A. Mrklas, North Olmsted, Ohio

[21] Appl. No.: 777,203

[22] Filed: Oct. 16, 1991

[51] Int. Cl.$^5$ ............................................. A61M 21/00
[52] U.S. Cl. ...................... 600/27; 434/236; 601/15
[58] Field of Search ............... 434/236, 237, 238; 600/26, 27, 28, 21; 128/24.1, 24.2, 24.3, 33, 32

[56] References Cited

U.S. PATENT DOCUMENTS

| | | | |
|---|---|---|---|
| 3,014,477 | 12/1961 | Carlin | 600/27 |
| 3,278,676 | 10/1966 | Becker | |
| 3,643,941 | 2/1972 | Kashar | 128/24.1 |
| 3,727,616 | 4/1973 | Lenzkes | |
| 3,753,433 | 8/1973 | Bakerich et al. | |
| 3,822,693 | 7/1974 | King | 600/27 |
| 3,826,250 | 7/1974 | Adams | |
| 3,837,331 | 9/1974 | Ross | |
| 3,967,616 | 7/1976 | Ross | |
| 4,258,706 | 3/1981 | Shank | 128/24.1 |
| 4,315,502 | 2/1982 | Gorges | |
| 4,335,710 | 6/1982 | Williamson | |
| 4,388,918 | 6/1983 | Filley | |
| 4,553,534 | 11/1985 | Stiegler | |
| 4,640,266 | 2/1987 | Levy | |
| 4,665,926 | 5/1987 | Launer et al. | |
| 4,728,293 | 3/1988 | Kole, Jr. | 434/236 |
| 4,736,307 | 4/1988 | Salb | |
| 4,893,615 | 1/1990 | Khabirova | 128/24.1 |
| 5,024,650 | 6/1991 | Hagiwara et al. | 128/24.1 |
| 5,036,858 | 8/1991 | Carter et al. | 600/27 |
| 5,076,281 | 12/1991 | Gavish | 600/28 |

FOREIGN PATENT DOCUMENTS

| | | | |
|---|---|---|---|
| 3447105 | 7/1985 | Fed. Rep. of Germany | 600/27 |
| 3823402 | 1/1990 | Fed. Rep. of Germany | 600/28 |
| 1119700 | 10/1984 | U.S.S.R. | 128/24.1 |
| 2201599 | 9/1988 | United Kingdom | 600/26 |
| 0004191 | 5/1989 | World Int. Prop. O. | 600/27 |

*Primary Examiner*—Jessica J. Harrison
*Attorney, Agent, or Firm*—Sixbey, Friedman, Leedom & Ferguson

[57] ABSTRACT

An integrated stress reduction system detects the stress level of a subject and displays a light pattern reflecting the relationship between the subject's stress level and a target level. At the same time, the system provides relaxing visual, sound, tactile, environmental, and other effects to aid the subject in reducing his or her stress level to the target level. In one preferred embodiment, the intensity, type, and duration of the relaxing effects are controlled by a computer program in response to the measured stress level. The light pattern stress level display uses a laser which is deflected on one axis by a measured stress level signal and on a second axis perpendicular to the first by a target signal representing the target stress level. The pattern produced is more complex when the two signals do not coincide, and becomes a less complex geometric figure as the subject's stress level approaches the target.

25 Claims, 9 Drawing Sheets

STRESS REDUCTION SYSTEM AND METHOD

BACKGROUND OF THE INVENTION

The present invention relates to an apparatus and method for reducing stress in a human subject through the production of soothing audio, visual and other sensory effects.

In today's society, men and women live active and often very stressful lives People frequently fail to take the time to relax and, as a result, stress builds up without release causing a variety of physiological and psychological problems. Research has shown that stress can be reduced through the alteration of brain wave patterns which the brain utilizes in order to function. Stimuli such as sound and light can affect and actually alter the flow of these brain wave patterns.

Biofeedback systems are well known in the art for use in detecting levels of stress in subjects and providing the appropriate stimuli to affect and alter the flow of brain wave patterns The biofeedback system monitors and processes bioelectrical signals generated in specific topological regions of a subject's nervous system and produces a sensory stimulus if the system detects the presence or absence of certain characteristics in the signal's wave form patterns. These characteristics may be correlated with a certain desired condition of the subject's nervous system. The sensory stimulus provided by the biofeedback system, typically an audio or visual stimulus, or combination thereof, is fed back to the subject which associates the presence of the stimulus with the goal of achieving the desired condition of its nervous system. By responding to the stimulus, the subject can be trained to control the waveform patterns of the monitored bioelectrical signals and thereby control his or her own nervous system. Such a system is illustrated in U.S. Pat. No. 3,727,616 to Ross.

Because biofeedback devices operate on the basis of internal stimuli, that is, stimuli produced in response to bioelectrical signals generated by the subject, the success of the true biofeedback device is dependent upon a subject attempting to consciously control his or her state of stress. Many people cannot effect such control over their involuntary nervous systems. In addition, biofeedback systems are traditionally quite expensive and require complex equipment.

Prior art devices have attempted to overcome these drawbacks by producing a state of mental harmonization or relaxation in a subject without detecting the subject's state of stress, that is, through the use of a program of external stimuli. In the apparatus and method shown in U.S. Pat. No. 4,553,534 to Stiegler, the subject wears a specially designed helmet through which a programmed combination of lights, colors, words and music is transmitted. U.S. Pat. No. 4,315,502 to Gorges illustrates another type of device for stimulating brain function which does not rely upon a subject's internal stimulus. The device provides stimulation and coordination of whole brain wave function through a combined source of pulsating light in an eye covering mask which locates the light sources adjacent the left and right eyes of a subject and an audio headset which applies sound signals to the left and right ears of the subject. U.S. Pat. Nos. 3,826,250 to Adams and 4,640,266 to Levy show systems providing an enclosed chamber in which the subject sits while various stimuli are provided through loudspeakers or on visual displays. However, because none of the above-mentioned systems provide a stress detection method, the stimuli cannot be tailored to a subject's changing state of stress and individual needs.

There is a need for an improved method and apparatus for reducing physiological and psychological stress in people which is readily available to the general public at an affordable cost, which is computer-controllable, which exposes the subject to a fully choreographed stress reduction session, which detects the subject's state of stress and modifies the session in response to any changes, and which effectively reduces stress in the subject without the requirement that the subject effect control over his or her involuntary nervous system.

SUMMARY OF THE INVENTION

A primary object of this invention is to provide a comprehensive stress reduction system for use by the general public.

A further object of the invention is to provide a standalone comprehensive stress reduction system that simultaneously exposes the subject to several different types of sensory phenomena, each designed to produce a relaxing effect.

Another object of the invention is to provide a computer-controlled stress reduction system which orchestrates a fully-choreographed stress reduction session.

It is another object of the invention to provide a computer-controlled system that uses biological sensors to aid the computer in controlling sensory stimuli in response to the subject stress level to thus choreograph a stress reduction session.

A further object of the invention is to provide a relaxation system wherein a subject is supported in an isolating private enclosure also providing sensory stimulation equipment and a stress level indicator.

Another object of the invention is to provide a stress reduction facility with a plurality of subject enclosures controlled and monitored from a central operator station.

Yet another object of the invention is to provide a novel system for reducing stress levels having a stress level indicator viewable by a subject which indicates stress level to the subject using a light pattern having complexity related to the stress level.

A further object of the present invention is to provide a laser light pattern generator for a stress reduction system.

Another object of the present invention is to provide a laser light pattern generator useful in a stress reduction system having motion controlled on a plurality of axes.

It is also an object of the invention to provide a stress reduction system which displays stress levels using a laser beam deflected in a first axis according to a measured stress level signal and deflected in a second axis according to a target stress level signal.

Yet another object of the present invention is to provide a stress reduction system having a single used both for displaying general relaxing light patterns and for displaying a particular light pattern having complexity related to the difference between a measured stress level and a target stress level.

A further object of the present invention is to provide a stress reduction system which uses a woven fiber optic fabric to display relaxing color patterns.

Another object of the present invention is to provide a method of reducing stress in a subject using apparatus constructed according to the previously mentioned objects of the invention.

It is also an object of the invention to provide a method of reducing stress in a subject in which the subject is placed in a comfortable supported position, where the stress level of the subject can be continuously monitored, and a continuous relaxing visual indication of the stress level is provided using a light pattern with a pattern complexity related to the stress level, while other relaxing sensory stimulation is applied to the subject.

Another object of the invention is to provide a method of reducing stress in a subject in which a laser is used to provide a patterned visual indication of measured stress level in relation to a target level.

These objects and others are achieved in an integrated stress reduction system which detects the stress level of a subject and displays a light pattern reflecting the relationship between the subject's stress level and a target level. At the same time, the system provides relaxing visual, sound, tactile, environmental, and other effects to aid the subject in reducing his or her stress level to the target level. In one preferred embodiment, the intensity, type, and duration of the relaxing effects are controlled by a computer program in response to the measured stress level. The light pattern stress level display uses a laser which is deflected on one axis by a measured stress level signal and on a second axis perpendicular to the first by a target signal representing the target stress level. The pattern produced will be more complex when the two signals do not coincide, and will become a less complex geometric figure as the subject's stress level approaches the target.

DETAILED DESCRIPTION OF THE PREFERRED EMBODIMENT

Figure 1A:
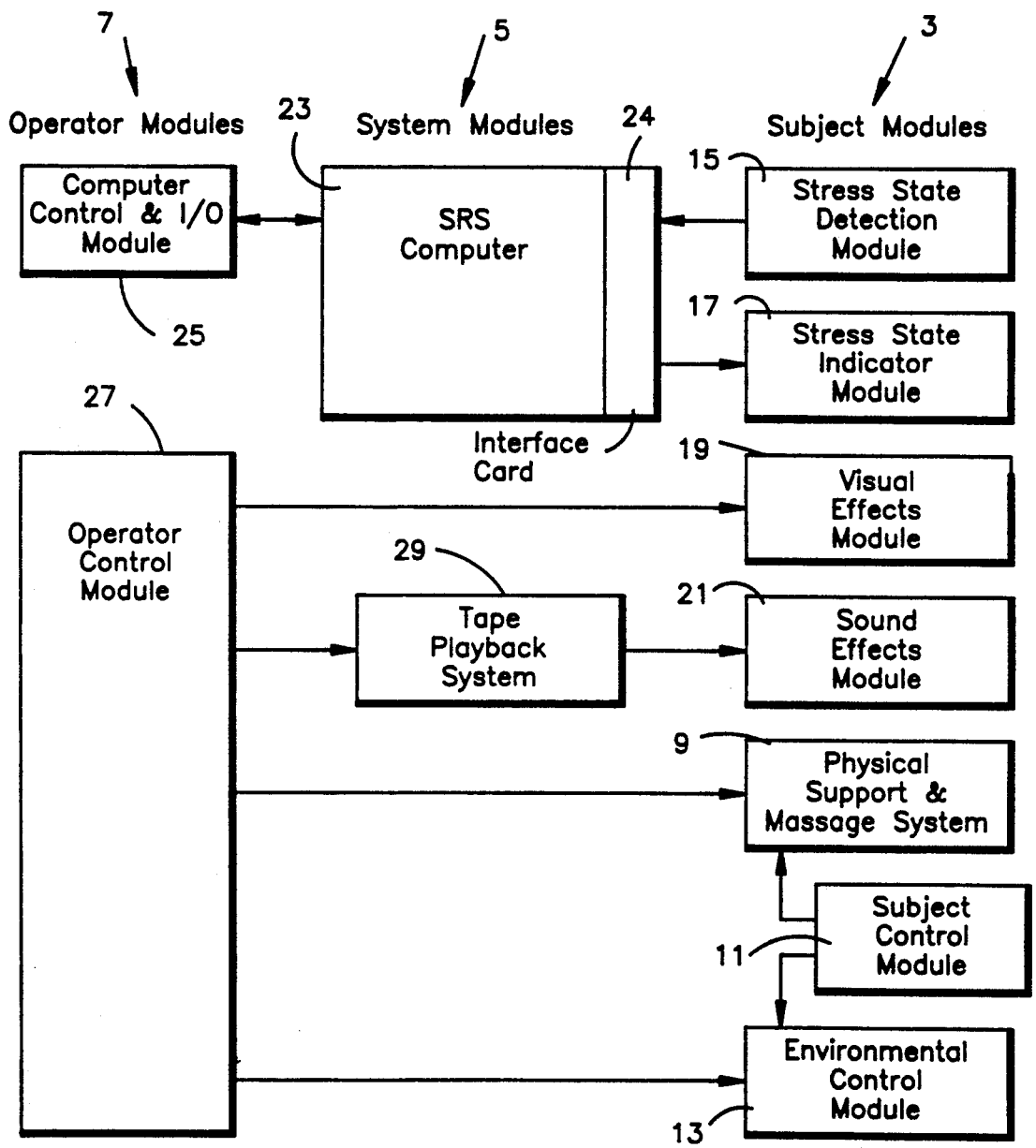
FIG. 1A is a block diagram of the basic system of the present invention.

The present invention is an integrated system for reducing stress. The components of this system are shown generally in the separate embodiments of FIGS. 1A and 1B, which are block diagrams of the Stress Reduction System (SRS) 1. Referring now to FIG. 1A, in its first embodiment, the system includes generally subject modules 3, system modules 5 and operator modules 7. The subject modules 3 include a physical support and massage module 9, a subject control module 11, an environmental control module 13, a stress state detection module 15, a stress state indicator module 17, a visual effects module 19 and a sound effects module 21. The operator Modules 7 include computer control and I/O module 25 and operator control module 27. The operator modules 7 are modules that are controlled by and provide indications to the operator, to form an operator interface. The subject modules 3 are modules that interface with the subject or client to produce soothing audio, visual, and other sensory effects and to monitor the subject's relaxation state, and are thus means for providing sensory stimulation. The system modules 5 are intermediate control and signal generation modules in the circuit between the subject modules 3 and the operator modules 7.

In this embodiment the operator control module provides a means for controlling most of the Subject Modules 3 in the SRS 1. The operator control module 27 includes an instrument panel having various switches, dials, control knobs, indicator lamps and other devices mounted on the instrument panel of operator control module 27 and connected by wires and cables to the modules which they control. Other desired connection means other than conventional wiring may be used, such as optical fiber data cables, radio waves, or infrared transmissions. The System Modules 5 may include a tape playback system 29 in addition to the SRS computer 23. In the embodiment of FIG. 1A, an operator will usually be required to actively monitor the entire session and manipulate controls as needed. This embodiment thus requires substantial attention from a trained operator to control the operation of subject modules 3 to thus choreograph a relaxation session.

Figure 1B:
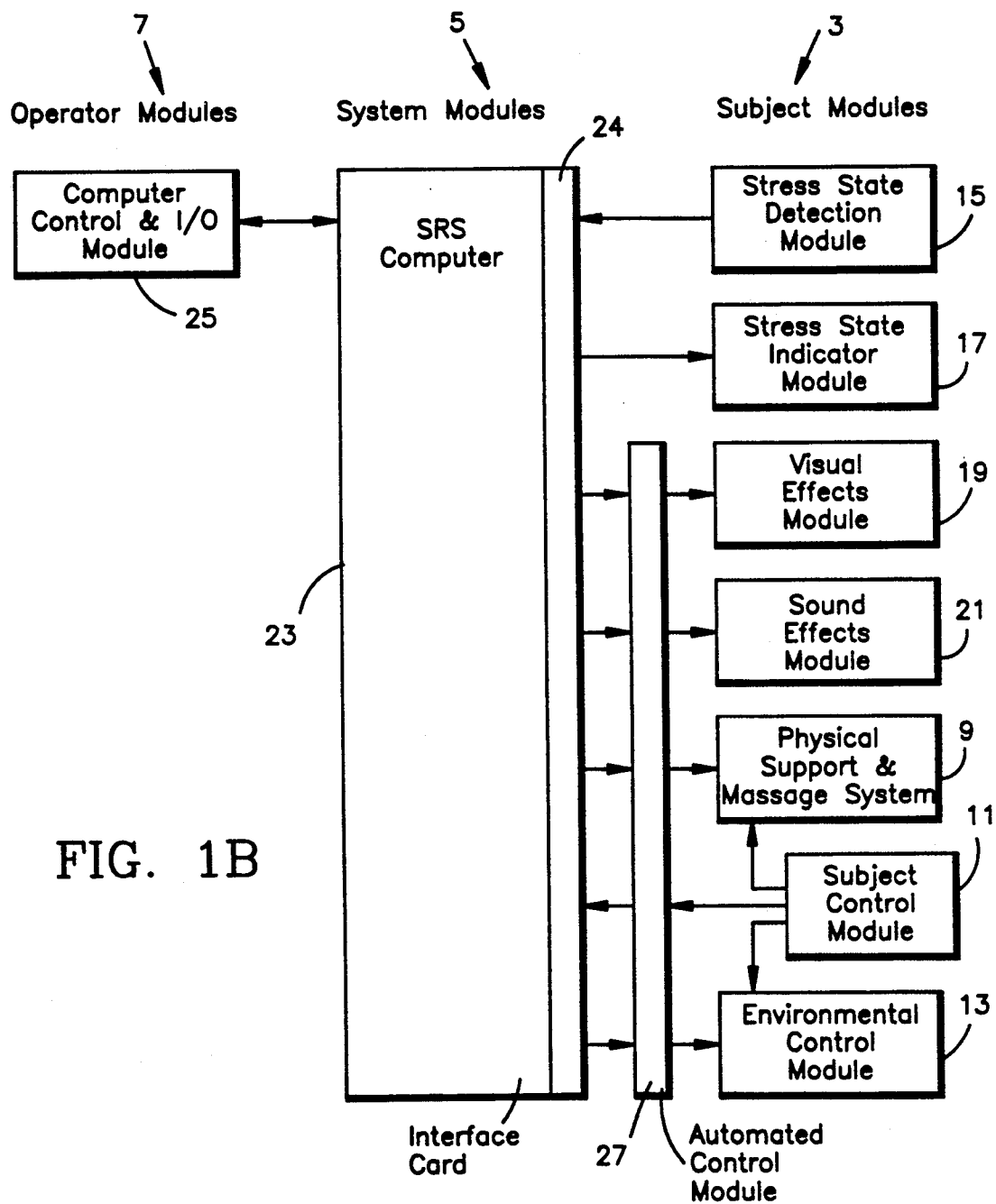
FIG. 1B is a block diagram of an alternate embodiment of the system of FIG. 1A incorporating full computer control of the stress reduction system according to the present invention using an automated control module.

FIG. 1B illustrates another, more preferred, embodiment of the invention which is a fully automated, version of the SRS 1 shown in FIG. 1A wherein the SRS computer 23 is used as a means for controlling the subject modules 3. In this version, the Subject Modules 3 interface directly with the System Modules 5, namely, the SRS computer 23, by means of a printed circuit hardware interface card 24. The interface card 24 provides an analog and digital interface and serves to digitize the incoming signals, such as those from the stress state detection module 15 and subject control module 11, give the signals the proper voltage and format to interface the signals with the SRS computer 23, and enter the data in certain reserved memory locations within the card 24 or the SRS computer 23. The interface card 24 can also be used to send computer signals out to the modules of subject modules 3, such as the stress state indicator module 17, visual effects module 19 and sound effects module 21. The physical support and massage module 9 and environmenval control module 13 may be controlled by either the SRS computer 23 or the subject control module 11 or both, as will be described later in more detail. The Operator Modules 7, namely the computer control and I/O module 25, interface directly with the SRS computer 23. The computer control and I/O module 25 includes the peripheral devices typically connected to a computer to perform the required input and output functions, such as a printer, keyboard, hard disk drive, floppy disk drive, monitor screen, mouse, power conditioner unit and the like. In a completely automated system, the operator need only take a few minutes to make client entries in the SRS computer 23 at the beginning of a session and then start the programs. Thereafter, the operator may attend to other clients.

The SRS computer 23 in all embodiments may be an IBM AT or similar computer and includes software which, through a conventional interface card, detects signals from the stress state detection module 15 and provides output signals to the stress state indicator module 17.

Figure 2:
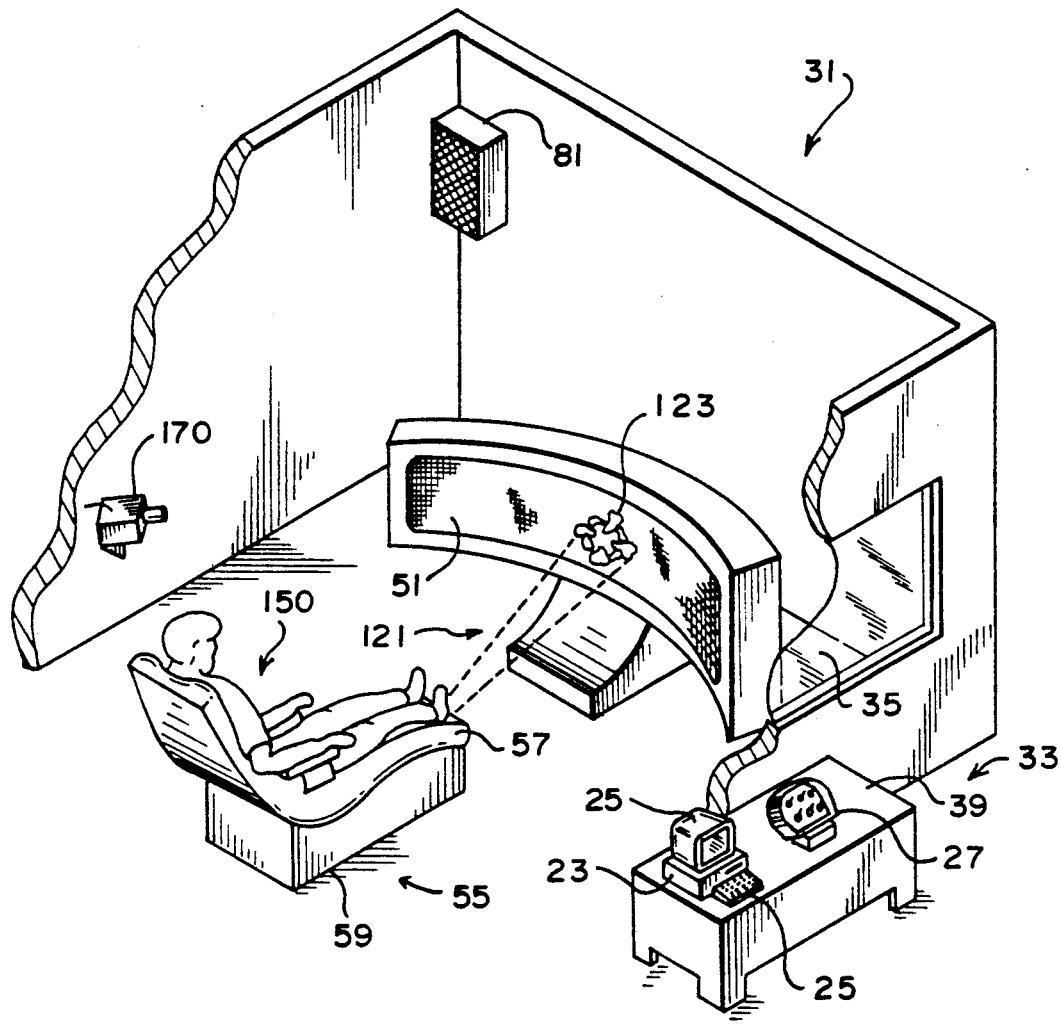
FIG. 2 is a perspective view of the stress reduction system of the present invention installed in a dedicated subject room.

FIG. 2 shows the preferred physical arrangement of the SRS 1, in which the Subject Modules 3 are housed in the subject room 31, constructed to serve as a dedicated private booth, while the System Modules 5 and Operator Modules 7 are placed in an adjacent operator control room 33 with a window or one-way mirror 35 separating the two rooms. In a large facility, there may be a number of subject rooms 31 arranged in a semicircle adjacent to a single operator control room 33. The subject room 31 is preferably a minimum of 10 feet by 12 feet with 8 foot acoustic tile ceilings and a 30 inch solid wood door (not shown). The floor and at least one wall are preferably carpeted or provided with other sound-deadening materials to reduce sound reflection. The remaining three walls are covered with any desired type of material.

Figure 6:
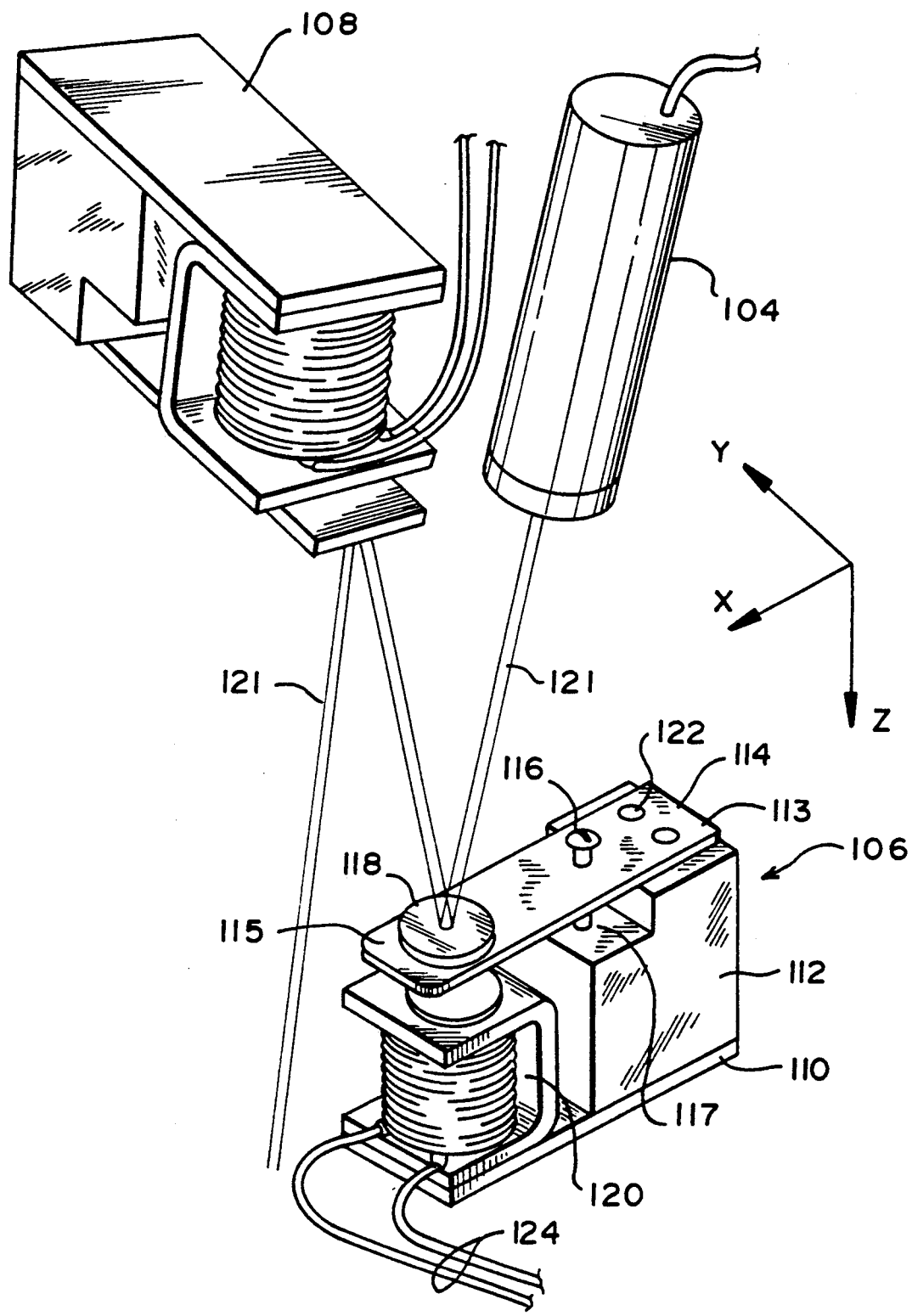
FIG. 6 is an assembly drawing showing a laser beam projecting apparatus for projecting waveforms of interest according to the present invention.

The subject room 31 also houses a subject chair 55 for supporting the subject 150. The subject chair 55 has a base 59 and a seating surface 57. A laser projection system, which will be described later in more detail with reference to FIG. 6, is located in the base 59 of subject chair 55 and projects laser beam 121 on screen 51 to form a Lissajous pattern 123 on the screen 51. Speakers 81 are also provided in subject room 31, and, optionally, a projector 170.

Figure 3:
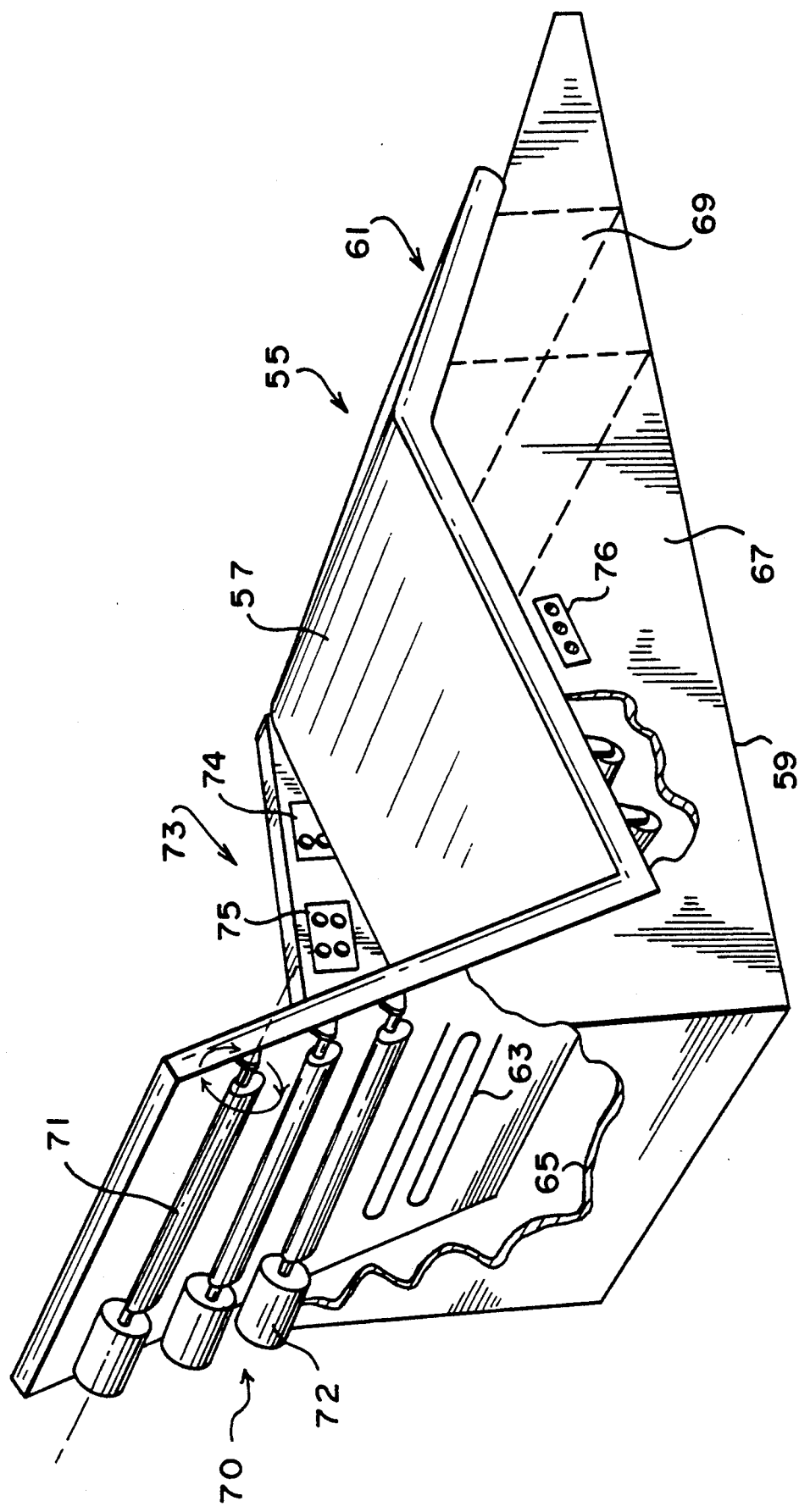
FIG. 3 is an assembly drawing of a relaxation chair used in the system of the present invention.

FIG. 3 shows the subject chair 55 in detail. The subject chair 55 preferably incorporates physical support and massage module 9, subject control module 11 and portions of environmental control module 13. Thus, the subject chair 55 provides a support aspect, a massage aspect, a subject control aspect, and an environmental control aspect. As noted previously, subject chair 55 has a seating surface 57 and a base unit 59. Subject chair 55 also has a foot end 61, outside surface 67, and a compartment 69 located in the base unit 59 to house a laser and laser aiming unit (not shown). The subject chair 55 may also include associated cushions, canopies, curtained enclosure, rocking mechanisms, spring mounts, arm rests, separate feet support, self illuminating controls, instruction manual holder, ashtrays, tissue paper holders, fragrance dispensers, built-in water-filled cushioning, and other comfort modifications which do not have adjustments or controls. The subject chair 55 may also be equipped with high voltage, low current electrical stimulation pads to stimulate muscles.

Heating elements 63 are provided in the subject chair 55 as part of the environment control module 13. A plurality of heating elements 63, which may be electrical heating pads or infrared radiant heating elements, are located in various desirable locations under the seating surface 57. In general, heating elements 63 will be provided under substantially all of the seating surface 57 to provide uniform warmth to the subject. If desired, the heating elements 63 could also be located to provide more heat in the foot, back, or other desired areas and less heat or no heat in other areas such as the head and rump areas.

The physical support aspect of the subject chair 55 is provided by the seating surface 57. The subject chair 55 is designed like a lounge chair and will support the subject 150 without putting him to sleep or distracting him from viewing of the screen 51 (shown in FIG. 2). The seating surface 57 is approximately six feet long and thirty inches wide. The seating surface 57 is fully padded and covered. The base unit 59 is approximately seven feet long and extends to within three inches of the floor at the foot end 61 of the subject chair 55. The base unit 59 is constructed using a hardwood frame (not shown) and plywood sides 65. The outside surface 67 is covered in plastic laminate and painted to match the screen support 85 and housing 87. The chair 55 also contains jacks 76 for conventional headphones which connect to the tape playback system 29 located at the operator control module 27, and also for connection of biofeedback probes worn by subject 150 to the stress state detection module 15. A plurality of jacks 76 are provided depending on the connection requirements of the probes and headphones used.

The massage aspect of the subject chair 55 is provided in the preferred embodiment by a series of vibrating rod-like elements 70 which are positioned horizontally in the subject chair 55 from the region of the subject's neck down to his feet. For clarity, only a few vibrating rod-like elements 70 are shown in the drawing figure, but there are preferably a large number of vibrating rod-like elements 70 located substantially continuously from the neck area to the foot area under seating surface 57. The vibrating rod-like elements 70 each comprise a motor 72 driving a roller 71 mounted off-center along its axis so that the rollers 71 move repetitively closer and further from the subject s back during rotation through a full circle by the motor 72. Preferably, each vibrating rod-like element 70 is individually controllable. However, if desired, the rod-like elements 70 could be controlled in groups, with a single motor arranged to drive each group of vibrating rod-like elements 70. Vibrating rod-like elements 70 can be turned on or off by the SRS computer 23 in the embodiment of FIG. 1B or, in the embodiment of FIG. 1A, by the operator control module 27. The amplitude or speed of vibration can be controlled by the subject through conveniently positioned mechanical comfort controls 75. The subject may select a high rate of vibration or reduce it to zero, but the SRS computer 23 or operator control module 27 turns the rod-like elements 70 on and off. Simplified versions of the subject chair 55 may include only one or a few vibrating elements using only one or a few electric motors.

During the course of a session, the vibrating rod-like elements 70 located at the foot end 61 may be turned on initially. As the session progresses, the first group of vibrating rod-like elements 70 may be turned off and the next group of vibrating rod-like elements 70 turned on in sequence, moving towards the subject's neck region. In the embodiment of FIG. 1B, The SRS computer 23 may time the moving region of massaging vibrations to take five minutes to travel the length of the subject's body. Afterwards, the SRS computer 23 may turn on all the vibrating rod-like elements 70 to give the subject a full massage for a few minutes. The SRS computer 23 may again initiate the massage mechanism near the end of the session to awaken the subject from his relaxed state and into normal wakefulness. The SRS computer 23 may, of course, be programmed to follow other massage sequences during a session depending on the objectives of the session, or the massage sequence could be controlled manually in the embodiment of FIG. 1A.

The subject control and environmental control aspects of the subject chair 55 are provided by controls of subject control module 11 associated with the subject chair 55. Specifically, the subject control module 11 includes subject controls 73 which may be installed on the subject chair 55 for access by the subject. The subject controls 73 include mechanical comfort controls 75 which operate various position settings of the subject chair 55 and the associated massage devices, and environment controls 74 to regulate room conditions and heating elements 63. The environmental controls 74 may include thermostats, on/off switches, airflow controls, humidity controls, and other like environmental controls. The mechanical comfort controls 75 provide functional control of physical support and massage module 9. The subject controls 73 are either mechanical, electrical or both, operated by the subject to maximize his state of comfort and relaxation. The subject chair 55 may have one or more mechanical comfort controls 75 to reposition the reclining angle, feet position, head position, height above floor, orientation of chair, degree of padding resiliency, and other adjustments to the subject chair 55. The mechanical comfort controls 75 are mounted at convenient positions on or near the subject chair 55 to allow the subject to configure the subject chair 55 to a comfortable position. The mechanical comfort controls 75 may be directly connected to control the vibrating elements 70 and the chair position or may have sensors which feed indications of control switch and dial positions to the SRS computer 23 for fully computerized control of support, massage, and environmental equipment through the SRS computer 23. If the subject chair 55 is equipped with powered position adjustment devices, such as electrical or hydraulic elevation and bladder inflation devices, rather than having purely mechanical adjustments, the adjustment devices can be controlled through comfort controls 75 or by the SRS computer 23 in response to indications of comfort controls 75.

Figure 4:
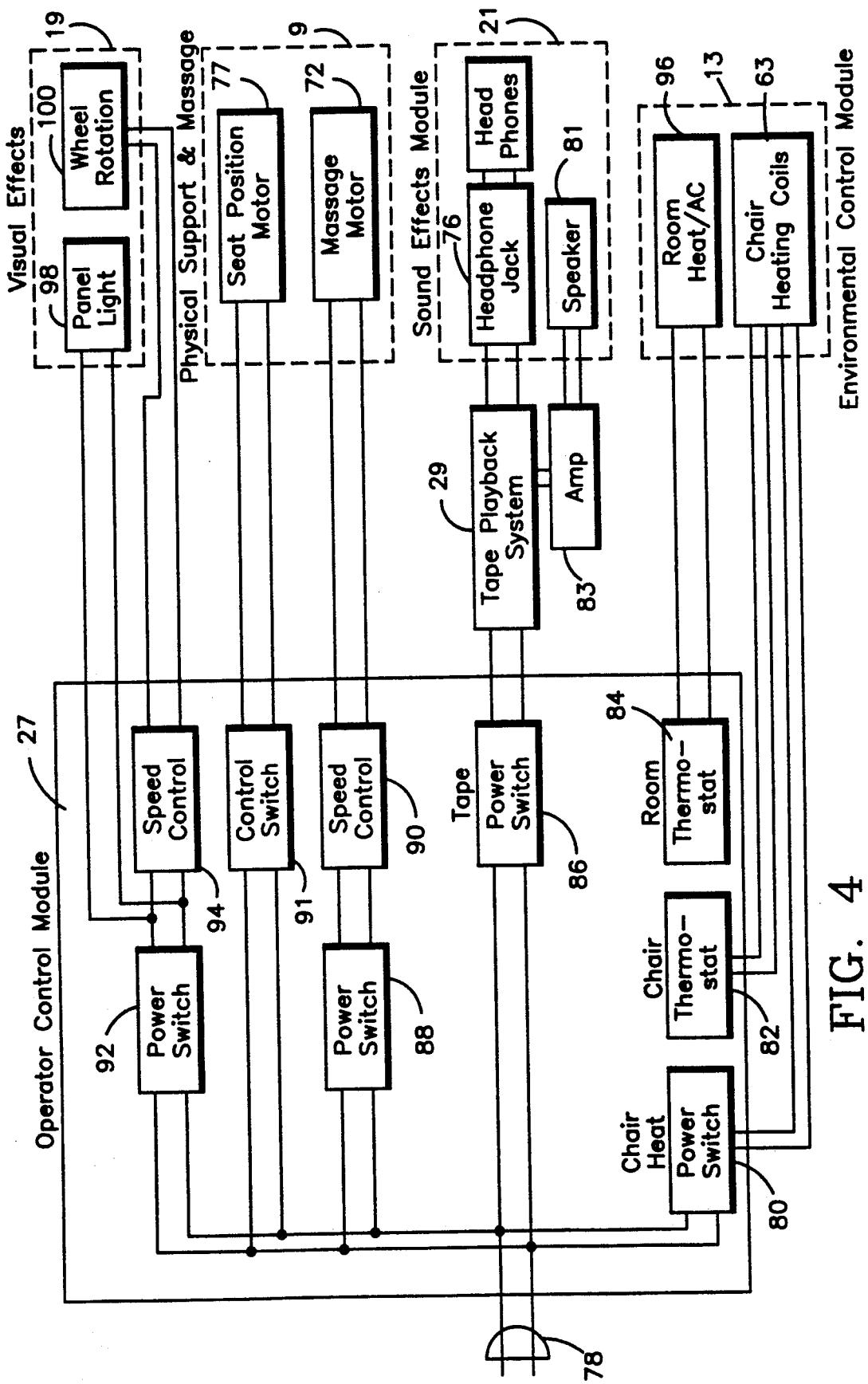
FIG. 4 is a block circuit diagram of the operator control module of the present invention used with the embodiment of FIG. 1A.

In the manually-controlled embodiment of FIG. 1A, the operator control module 27 takes the form of a pedestal-like console that sits on a desktop 39, along with the SRS computer 23, in the operator control room 33 (all shown in FIG. 2). The operator control module 27 contains switches, potentiometers, and other controls necessary to control the operation of visual effects module 19, sound effects module 21, physical support and massage system 9, and environmental control module 13. The circuitry of the operator control module 27 will be described in detail with reference to FIG. 4. As shown in FIG. 4, the operator control module 27 includes power source 78, chair heat switch 80, chair thermostat 82, room thermostat 84, tape power switch 86 of tape playback system 29, massage power switches 88, massage speed control 90, seat position motor control switch 91, visual effects power switch 92, and visual effects speed control 94. Power switches 80, 88, 91 and 92 control the connection of power source 78 to chair heating coils 63, massage motors 72, seat position motors 77, and visual effects module 19, respectively. The power source 78 may be 120 VAC household power or another power source. If some of the modules controlled by operator control module 27 operate using a power source other than the power source 78, suitable rectification and voltage level conversion may be performed for those modules, within operator control module 27, in a manner well-known in the art.

The controls in operator control module 27 for the environmental control module 13 include chair heat switch 80, chair thermostat 82, and room thermostat 84. The chair thermostat 82 will be connected to control the chair heating coils 63. Although for simplicity only one chair heat switch 80 and one chair thermostat 82 is shown, plural chair heat switches 80 and chair thermostats 82 will be used if there are plural chair heating coils 63 and individual control of these plural chair heating coils 63 is desired. The room thermostat 84 is connected to a room heating and air conditioning system 96 associated with subject room 31 (shown in FIG. 2) to control the temperature in the subject room 31. The room thermostat 84 may also incorporate other environmental controls, such as fan controls and humidity controls, responded to by room heating and air conditioning system 96 to control the environment of subject room 31. Thus, the controls of operator control module 27 provide control of the environmental control module 13, including room heating and air conditioning system 96 and chair heating coils 63. As shown in FIG. 2, using operator control module 27, the operator can selectively provide direct radiant heat through the chair surface 57 to the subject 150, as well as providing complete control of temperature, air flow, and humidity generally in the subject room 31. As described previously in the text accompanying FIG. 3, environment controls 74 performing the functions of power switch 80 and thermostats 82 and 84 may be provided directly on the subject chair 55. Environmental controls 74 on subject chair 55 may operate in parallel with or may entirely replace the environmental controls in operator control module 27.

In the preferred embodiment, the environmental control module (ECM) 13 may also control the intensity and/or color of booth background lighting, and release of preferred fragrances into booth air to provide a relaxing olfactory stimulus, and appropriate controls may be provided for these functions both in control module 27 or 27' and in subject controls 73, connected in a manner like that described for the other environmental controls.

Referring again to FIG. 4, the operator control module 27 also provides control of the sound effects module 21. The tape power switch 86 selectively connects power from power source 78 to tape playback system 29. Tape playback system 29 is connected to headphone jack 76 and may also be connected through an amplifier 83 to speakers 81 in subject room 31 (shown in FIG. 2). The tape power switch 86 activates the tape playback system 29 to provide amplified taped sounds or music at headphone jack 76, speakers 81, or both depending on subject preference. The amplifier 83 is shown connected directly to tape playback system 29, so that switching between output to headphone jack 76 and speaker 81 is controlled internal to tape playback system 29. However, control of output switching and output signal level (volume) can be accomplished through controls in operator control module 27 if desired. In one preferred embodiment, tape playback system 29 and amplifier 83 comprise a suitable conventional stereo cassette tape deck, amplifier, and headphone/speaker output switching mechanism which are built into the console of operator control module 27. In this manner, controls for the tape playback system 29 and amplifier 83, including on/off controls, stop, play, fast-forward and rewind, volume, balance, and program controls, as well as other controls commonly desired for controlling stereo sound output, are provided at the console of operator control module 27 for ready access by the operator. It will usually be desirable to provide a volume control accessible to the subject, such as on subject chair 55, for adjusting the sound level provided by sound effects module 21.

In lieu of a cassette tape system, the sound effects module 21 may also incorporate an optical disk or other random access information storage media which stores prerecorded tracks of music, tranquil sounds, and verbal, subliminal, or supraliminal suggestions of relaxation. The SRS computer 23 may be programmed to select tracks of tranquil sounds or music and combine them with verbal, subliminal and supraliminal suggestions, and electronically pass the information through headphone jack 76 or speaker system 81 to the subject.

The physical support and massage module 9 is controlled by massage motor power switch 88, massage motor speed control 90, and seat position motor control switch 91. Power switch 88 and speed control 90 are connected in series between power source 78 and a massage motor or motors 72. Only one set of these controls is shown, but if separate control of a plurality of massage motors 72 is desired, several sets of controls 88 and/or 90 will be installed in operator control module 27. The control switch 91 is connected between power source 78 and seat position motor 77. Again, there may be a plurality of seat position motors 77 for which a number of control switches 91 will be provided. Seat position motors 77 may include motors connected to tilt portions of the seating surface 57 (shown in FIG. 3) in desired directions, and motors connected to mechanisms that change the contour, flexibility, or rigidity of the seating surface 57, such as lumbar support position controls and inflater controls. Suitable mechanisms and motors which can be fitted in a known manner to the subject chair 55 for providing the described functions of seat position motors 77 can be found in automotive seating applications, adjustable home and hospital beds, household easy chairs, and the like. Thus, through the operator control module 27, the operator can fully control the physical support and massage module 9, including the amount and position of massage activity, the seating position, and the firmness of support in areas of the seating surface 57 where adjustments are provided. As described previously, similar controls may also be provided directly on the subject chair 55 in the form of mechanical comfort controls 75 (shown in FIG. 3). The mechanical comfort controls 75 can either duplicate or replace entirely the controls in operator control module 27 for physical support and massage module 9. In the preferred embodiment, at least the controls for massage motors 72 will be provided at the operator control module 27 since it will be desirable to vary the level and location of massage during a session.

Controls in operator control module 27 are also provided for controlling visual effects module 19. In the preferred embodiment, a main visual effects power switch 92 is connected to the power source 78 and is also connected to selectively apply power to panel light 98 and speed control 94. The speed control 94 is connected to a wheel rotation motor 100 to provide power to wheel rotation motor 100 and to control the rotational speed thereof. The power switch 92 thus activates the panel light 98 and the wheel rotation motor 100, and the speed control 94 controls the rotational speed of the wheel rotation motor 100 Visual effects module 19 may optionally include the projector 170. When projector 170 is present, control circuits for activating the projector 170 (not shown) will be provided, similar to the control circuits shown for the other visual effects devices Projector 170 may be a kaleidoscopic pattern projector and/or a constellation or a points-of-light (star) projector. When actuated, depending on its design, projector 170 will project onto the screen 51 a still or moving pattern such as a kaleidoscope-type pattern or a "night sky" pattern of stars or constellations.

Figure 5:
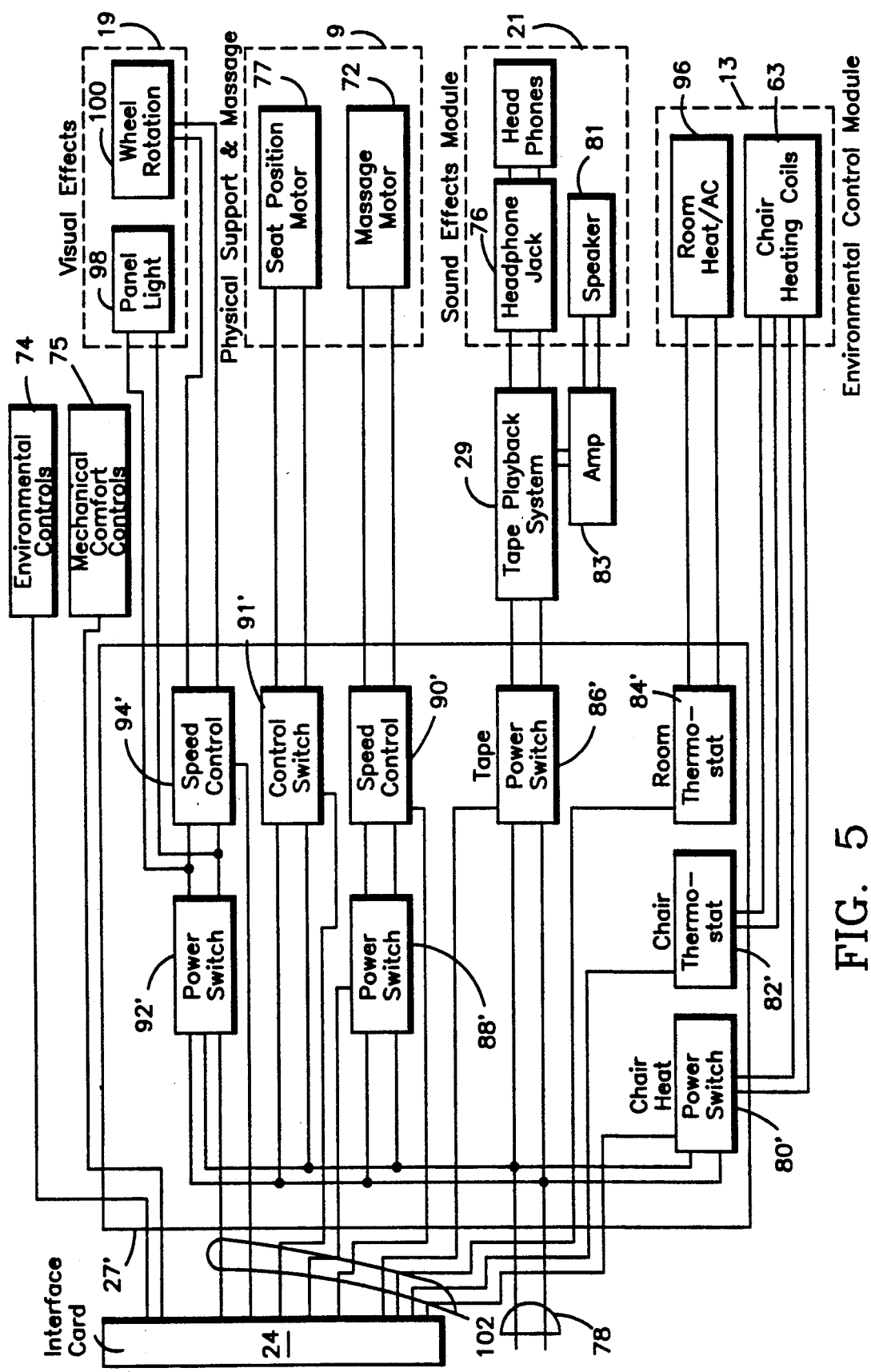
FIG. 5 is a block circuit diagram of the automated control module used with the embodiment of FIG. 1B.

As noted previously, in the automated embodiment of FIG. 1B, the control functions of the operator control module 27 which have been described in detail with reference to FIG. 4 are performed by the SRS computer 23 acting through an interface card 24 connected to an automated control module 27'. This arrangement is shown in FIG. 5. In the embodiment of FIG. 5, used in the system of FIG. 1B, the SRS computer 23 will interface with and control the subject modules 3 according to a predefined program. In this embodiment, control circuitry is provided in automated control module 27' which is essentially analogous to the control circuitry of operator control module 27 shown in FIG. 4. Elements in FIG. 5 indicated by "prime" reference numerals perform the same control functions as the elements with analogous reference numerals in FIG. 4. However, input and output ports of interface card 24 will be connected to each of the control devices 80', 82', 84', 86', 88', 90', 91', 92', and 94' by control lines 102. The power switches 80', 86', 88', 91', and 92', the speed controls 90' and 94', and the thermostats 82' and 84' used in the fully automated embodiment of FIG. 1B will be of the type designed to work with low-voltage electronic controls, i.e. responsive to low-voltage digital or analog signals transmitted from interface card 24 on the control lines 102 to perform the desired control functions, rather than being responsive to a hand movement of an operator such as flipping a switch or turning a dial. A single control line 102 is shown connecting an individual input and output port of interface card 24 and each of the control devices, but there may in some cases be more than one control line 102 running from interface card 24 to a particular control device depending on the requirements of the control device. For example, room thermostat 84 may have a plurality of control functions which might be controlled by a plurality of separate input and output ports on interface card 24. Alternatively, control devices in automated control module 27' which have internal processing capability may communicate with the SRS computer 23 using standardized parallel or serial interfaces located in the interface card 24 or otherwise associated with the SRS computer 23. Thus, the program of SRS computer 23 can control the modules 9, 13, 19, and 21 by sending certain signals to the appropriate input and output ports of interface card 24, with the signals calculated to cause the desired switching and control functions of the control devices of automated control module 27'.

Relatively simple software will be provided in SRS computer 23 to perform the desired control functions in response to a predefined session program. The software will perform at least the following functions: set specified controls after specified elapsed times, set controls to initial client preference defaults taken from a data file, and change control settings as a function of external variables such as measured stress level and time. Preferably, the software will operate using session program files in which the desired functions can be specified. For example, a program file for a session might consist of the following:

```
TURN ON STRESS STATE DETECTION MODULE AT TIME 0
TURN ON STRESS STATE INDICATOR MODULE AT TIME 0
TURN ON VISUAL EFFECTS MODULE AT TIME 0
SET WHEEL SPEED TO 10 AT TIME 0
TURN ON SOUND EFFECTS MODULE AT TIME 0
SET VOLUME TO CLIENT_VOLUME AT TIME 0
TURN ON GROUP 1 MASSAGE ROLLERS AT TIME 0
SET MASSAGE SPEED TO 10 AT TIME 0
TURN ON HEAT COILS AT TIME 0
SET HEAT COIL TEMPERATURE TO CLIENT_TEMP AT TIME 0
SET ROOM TEMPERATURE TO CLIENT_ROOM_TEMP AT TIME 0
VARY MASSAGE SPEED FROM 1 TO 10 WITH STRESS_PERCENTAGE
VARY WHEEL SPEED FROM 1 TO 10 WITH STRESS_PERCENTAGE
TURN OFF HEAT COILS WHEN STRESS_PERCENTAGE < 0.5
TURN ON GROUP 2 MASSAGE ROLLERS AT TIME 10 MIN
TURN OFF GROUP 1 MASSAGE ROLLERS AT TIME 10 MIN
TURN OFF ALL AT TIME 30 MIN
```

The software of SRS computer 23 can retrieve variables external to the session program file, such as the client preference defaults CLIENT_VOLUME, CLIENT_TEMP, and CLIENT_ROOM_TEMP. The software also receives from the SRS computer 23 the current time relative to the start of the session and the percentage of subject stress reduction that has occurred relative to a defined target. This percentage is calculated by retrieving an indication of the current stress level (CURRENT), retrieving the initially measured (higher) stress level at the beginning of the session (INITIAL), and retrieving the target stress level for the subject (TARGET) and using the following formula:

$$STRESS\_PERCENTAGE = \frac{CURRENT - TARGET}{INITIAL - TARGET}$$

In operation, the software merely scans the programmed commands in the session file repeatedly in sequence. For each command, the software will access any necessary external variables and perform calculations necessary to determine whether the programmed command requires a change in control signals that has not yet been executed. If so, the software generates the appropriate signals to the appropriate output ports. To illustrate, in the sample session program given above, the command SET ROOM TEMPERATURE TO CLIENT_ROOM_TEMP AT TIME 0 would cause the program to determine first whether the elapsed time is 0 minutes, and then whether or not the command was already executed at this time. If the command should be executed and has not been flagged as already executed, the software will retrieve the external variable CLIENT_ROOM_TEMP from a client preference data file for the particular subject and will generate signals to the appropriate output port to set the room temperature thermostat to the desired level. Commands such as VARY WHEEL SPEED FROM 1 TO 10 WITH STRESS_PERCENTAGE direct the software to continuously calculate the value of STRESS_PERCENTAGE as defined above and to set the speed of the wheel rotation motor 100 between defined levels proportionally to the current value of STRESS_PERCENTAGE. Thus, as the subject's stress level is reduced, the apparent motion of the visual effects of visual effects module 19 is reduced proportionally. Of course, other coding conventions for the session program file could be adopted within the scope of the invention, and other client preference variables and stress-based variables could be defined if desired.

The circuits shown in the embodiment of FIG. 5 respond to the signals produced by this software on the output ports of interface card 24. For example, the SRS computer 23 would be programmed to activate the panel light 98 at the beginning of a session in response to the TURN ON VISUAL EFFECTS MODULE AT TIME 0 command. The power switch 92' shown in FIG. 5 is a conventional power switching circuit of the type responding to a low-voltage digital signal to switch 120 VAC power from a power source. To turn the panel light 98 on, the program of SRS computer 23 will access the input and output port of interface card 24 that is associated with the power switch 92', initiating a change in the signal level (such as a transition from 0 VDC to 5 VDC) on the control line or lines 102 connecting interface card 24 and the power switch 92'. The power switch 92' will respond to this change in signal level to connect power source 78 to panel light 98, activating the panel light 98. The panel light 98 can also be turned off under control of SRS computer 23. To turn off panel light 98, the program of SRS computer 23 would write signals to interface card 24 directing that the input and output port associated with power switch 92' change from transmitting a 5 VDC signal to a 0 VDC signal. Power switch 92' will respond to this signal transition to halt the flow of current from power source 78 to panel light 98. Power switches 80', 86', 88', and 91' operate in a manner similar to the manner described for power switch 92' to control their respectively connected devices.

The speed controls 90' and 94' are "dimmer" or rheostat-type control circuits which operate in response to a low-current, variable-level DC signal to provide a varying power signal output, such as an AC power signal with varying peak voltage or an AC power signal with varying duty cycle. The speed controls 90' and 94' are connected through control lines 102 to respective analog output ports of interface card 24. These analog output ports can be controlled by the program of SRS computer 23 to provide a variable-voltage DC control signal output. Thus, the program of SRS computer 23 can selectively increase and decrease the operating speed of the various connected systems such as wheel rotation motor 100 and massage motors 72 during program execution.

Similarly, the thermostat controls 82' and 84' are connected to analog output ports of interface card 24 and receive therefrom a low-current, variable level DC signal indicative of desired temperature adjustments.

The thermostat controls 82' and 84' may be connected to several input and output ports of interface card 24, both digital and analog, to implement additional functions described previously such as fan speed control and humidity control. Alternatively, by selecting room heating and air conditioning systems 96 and/or chair heating coils 63 having internal control circuits operating with low-current DC control signals, the interface card 24 may be connected directly to these internal control circuits to effect control of the system 96 or coils 63 without additional automated controls in automated control module 27'. Others of the modules controlled through automated control module 27' may also be selected to operate directly from interface card 24.

In the SRS 1 embodiment of FIG. 1B, each of the mechanical comfort controls 75 on subject chair 55 is a sensor that sends information to the SRS computer 23 (through input ports of interface card 24) on its present setting, rather than directly controlling equipment. The control outputs which actually control the devices for which mechanical comfort controls 75 are provided may also be set by the SRS computer 23 independently of the inputs provided by subject 150 using the mechanical comfort controls 75. Usually the mechanical comfort controls 75 are operated by the subject during his initial SRS session and set to his most comfortable position. The SRS computer 23 will record these settings and during subsequent sessions, the SRS computer 23 sets the outputs corresponding to the signals from mechanical comfort controls 75 to the same position the subject had set them at the end of the proceeding session. The SRS computer 23 may also reset some of the control outputs during a session. For example, the subject chair 55 may be set to an upright position during the beginning of a session then slowly, incrementally repositioned to a reclining position as a state of deep relaxation is reached.

Similarly, in the fully-automatic embodiment of FIG. 1B, the environmental control module 13 may be controlled indirectly through SRS computer 23 by the environment controls 74 mounted on the subject chair 55 (shown in FIG. 3). These environment controls 74 are connected and operate in a manner similar to the mechanical comfort controls 75. All settings of the environment controls 74 selected by the subject are fed directly to the SRS computer 23 through interface card 24.

The SRS computer 23 records the preferred settings of environment controls 74 and mechanical comfort controls 75 in the client files for future reference and also sends signals to the appropriate devices to change the respective environmental conditions in the manner selected by the subject. In succeeding sessions, the SRS computer 23 will call up the client's environmental and comfort preferences from the computer memory and use them to set the environmental conditions according to these preferences as soon as the client's name is entered in the computer by the operator and the session begins. Whenever the client changes his environmental or comfort preferences, the SRS computer 23 makes the indicated changes and updates the client's files to reflect the new preferences. In the preferred embodiment, the environmental conditions may also be varied by the SRS computer 23 as part of the relaxation programming, independently of the subject's initial settings.

In simplified versions of the SRS 1 such as the embodiment of FIG. 1A, the environmental conditions may be under the direct control of the subject while seated in the subject chair 55 using simple mechanical and/or electrical environmental controls 74.

Referring again to FIGS. 1A and 1B, the stress state detection module 15 and the stress state indicator module 17 are connected to SRS computer 23 through interface card 24. Although not shown for clarity, suitable level and impedance interface circuitry will be provided between modules 15 and 17 and the interface card 24 depending on the design of these components. Such circuits may use suitable operational amplifiers or transistors to provide the signal levels and currents required by the circuits receiving the signals.

In the preferred embodiment, the stress detection module (SDM) 15 uses one or more of the following biological sensors: an expansion strap to measure breathing, a microphone to detect the heart beat, and electrode sensors to measure galvanometric skin resistance and brain wave activity Higher breathing rates and heart rate are associated with higher levels of stress, while lower breathing rates and heart rates are associated with lower levels of stress. The subject's state of stress may be calculated using one or more of these measurements. The biological sensors may be attached to the subject chair 55 or may be separately attachable to the subject. The sensors are connected to analog input and output ports of interface card 24 of SRS computer 23 by means of suitable conventional amplifying and signal generating circuitry which provides an electrical DC voltage signal with a level related to the breathing rate, heart rate, skin resistance, brainwaves, or other measured bodily function. When sensors are to be attached to the subject, leads for connecting the interface card 24 to the sensors will be provided at jacks 76 on subject chair 55 (shown in FIG. 3). Electrodes, microphones, and other sensors will be provided with a cable terminating in a plug compatible with the jacks 76. Suitable amplifying and signal generating circuitry is provided for each sensor to produce an electrical DC voltage signal at interface card 24, so that SRS computer 23 can read the ports of interface card 24 associated with the sensors of stress state detection module 15 to obtain stress state data.

The stress state indicator module 17 provides means for indicating the state of stress of the subject. Some subjects are able to consciously affect their state of stress, and information on the state of stress will be useful to these subjects. Other subjects, while unable to consciously affect their stress level, will find the display of stress state indicator module useful as an indicator of the amount of involuntary progress in relaxation resulting from the sensory stimulation provided by the present system. In a preferred embodiment, the stress indicator module includes a projected Lissajous pattern 123, with the shape and complexity of the pattern determined by the relationship between the present state of stress and a desired stress level. In the preferred embodiment, shown generally in FIG. 2, the pattern 123 is generated on a projection screen 51 using a laser beam 121 guided in a plurality of dimensions based on different signals for each dimension.

FIG. 6 shows the laser projection components of stress indicator module (SIM) 17. The projection components include a laser 104, a first steering mirror assembly 106, and a second steering mirror assembly 108. The laser 104 and steering mirror assemblies 106 and 108 are mounted in a vibration-absorbing housing (not shown) in precise relative positions. Preferably, adjusting screws, shims, or other adjustable mounting means (not shown) will be provided for mounting and aligning the components 104, 106, and 108 for proper interaction to project a laser beam 121 in a desired path. The steering mirror assemblies 106 and 108 are a means for guiding a laser beam simultaneously along a plurality of dimensions in response to input signals. The laser 104 may be any conventional laser of relatively low power. One suitable model is a hard-sealed helium-neon laser on the order of one milliwatt power with a beam diameter of 0.48 mm and divergence of 1.7. One suitable model is model ML811 sold by Metrologic of Bellmawr, N.J. The first and second steering mirror assemblies 106 and 108 are substantially identical except in the signals connected thereto, so that only the construction of the first steering mirror assembly 106 will be described in detail. The steering mirror assembly 106 comprises base 110, mounting block 112, spring 114, adjusting screw 116, mirror 118, electromagnet assembly 120, attaching means 122, and leads 124. Electromagnet assembly 120 and mounting block 112 are attached to the base 110. Mounting block 112 is a shaped structure of plastic, wood or other material. The electromagnet assembly 120 is an ordinary electromagnetic coil of the type used in small, inexpensive audio speakers and responds to signals on leads 124 to generate a field for moving One appropriate electromagnet assembly 120 is a 5 ounce magnet from a 3¼", 10 watt, 8 ohm audio speaker. The spring 114 comprises a short length of spring steel and has a mounted end 113 and a free end 115. Spring 114 should be coated on its underside, or top side, or both with silicon rubber for damping. The silicon rubber will tend to reduce continuing vibrations from prior signals to the electromagnet assembly, producing a pure vibrating output based substantially on the present signal on leads 124. The mounted end 113 of spring 114 is flexibly connected to mounting block 112 by attaching means 122 so that free end 115 of spring 114 lies in close proximity to the top of electromagnet assembly 120. Adjusting screw 116 is a means for adjusting the rest position of spring 114 to align the mirror 118 in a desired path for projecting laser beam 121. The adjusting screw 116 passes through a threaded hole in spring 114 so that, in the rest position of spring 114, the end 117 of adjusting screw 116 lies against mounting block 112. The mirror 118 is mounted on the free end 115 of spring 114 to move with the spring 114, responding to fields generated by electromagnet assembly 120 from signals on leads 124. The mirror 118 is a small, round first surface mirror; i.e., it is aluminized on the surface nearest the incident light. Light is reflected without passing through any glass, minimizing light loss and secondary refraction. As described previously, the vibration-absorbing housing containing the apparatus shown in FIG. 6 will be mounted in the compartment 69 of subject chair 55 (shown in FIG. 3) so that laser beam 121 is projected onto screen 51 (shown in FIG. 2).

The apparatus of FIG. 6 is connected to form a Lissajous pattern indicative of the subject's state of stress relative to a lower, target stress level. Specifically, biological information concerning the subject is digitized using an analog to digital (A/D) converter in an interface card associated with SRS computer 23 and is then fed to the SRS computer 23 for processing by computer software. A number of available biofeedback computer software programs are readily available, or a custom program could be provided to perform the functions required. A preferred computer software package is the Bio-Track program, version 4.0, sold by Expanded Technologies Incorporated, 3883 Greenway Place, Shreveport, La. 71105. The program and its operating manual, entitled "Bio-Track," are incorporated herein by reference. The preferred software can monitor up to four sensor channels providing signals indicative of the presence of certain conditions such as the presence of alpha brain waves, beta brain waves, relaxed breathing, low production of sweat or the like. The program generates an output signal respresentative of the subject's stress level, designated as an "audio output." In the present invention, this audio output signal is connected as an output through interface card 24 to the first steering mirror assembly 106. The SRS computer 23 simultaneously generates an "ideal" biological response signal on a second channel which is directed by appropriate electronic hardware to the second steering mirror assembly 108. The production of this signal will be described in more detail with reference to FIG. 7. The laser beam 121 strikes the two steering mirror assemblies 106 and 108 in quick succession at approximately perpendicular angles before beaming towards the screen 51. Using the coordinate system shown in the drawing figure, the laser beam 121 moves in the positive Z-direction; the first steering mirror assembly 106 responds to an actual stress level signal to cause the laser beam to deflect in the X-Z plane by a small angle. The second steering mirror assembly 108, placed as closely as possible to the first steering mirror assembly 106 along the path of the laser beam 121, causes the laser beam 121 to deflect in the Y-Z plane by a small angle in response to the ideal stress level signal.

Using this arrangement, if the same pure sinusoidal signal were transmitted to leads 124 of both steering mirror assemblies 106 and 108 simultaneously, the laser beam 121 would trace out an elliptical pattern on the screen 51. This pattern would be very nearly circular if the two steering mirrors 106, 119 were very close to one another along the optical path of the laser beam 121. Because of the persistence of vision of human sight, such a trace appears as a projected geometric figure to a human observer. Preferably, a potentiometer will be provided in the circuit between leads 124 and interface card 24 for adjusting the electronic signal strength entering the electromagnet assemblies 120. Using these potentiometers, the pattern can be adjusted to be completely circular for sinusoidal inputs. By adjusting the signal level provided to electromagnet assemblies 120, the potentiometers will vary the range of deflection of spring 114 and it is thus possible to adjust the overall size of the Lissajous pattern 123 as it appears on the screen 51. In the SRS 1, the electronic signal entering the first steering mirror assembly 106 is the amplified alpha wave signal, or the like, originating from the subject. The signal entering the second steering mirror assembly 108 is an "ideal" reference signal. The arrangement just described causes a circular-like pattern to be traced on the screen 51 by the laser beam when the alpha wave signal approaches the ideal reference signal; otherwise the pattern becomes a more complex closed pattern. The ideal reference signal could be an ideal alpha wave signal generated by the computer or it could be a recorded reference signal from the subject's rest state in a prior session offering a target that the subject can more easily achieve.

By observing the patterns, the subject may choose to consciously help himself achieve a more relaxed state by thinking thoughts and taking actions that result in a simpler and less fluctuating Lissajous pattern. The laser 104 is operated continuously during a session to project a continuously changing pattern of laser-produced light by beam 121 onto a screen 51 in front of the subject. The laser beam 121 is reflected between the electronically positioned steering mirrors 118 of steering mirror assemblies 106 and 108 which cause the light pattern to become simpler and more symmetrical as greater relaxation is achieved.

In other embodiments, the stress indicator module 17 may consist of a television or large screen monitor in place of the latter mechanism. The Lissajous pattern would then be imaged on the television screen. The television's Lissajous image could be in color to produce an appealing image. If the biological information is being sent to a television screen, then it is no longer necessary to image the information as Lissajous curves; the information could be portrayed as moving swirls of color that become calmer as the subject relaxes. Alternatively, images of a storm could be shown when the subject is under stress where the storm scenes become calmer and diminish to clear skies and calm seas when the subject is relaxed, or any other non-quantitative graphical representation of stress and calm states could be used in a computer controlled television SIM 17. In other preferred embodiments, the SIM 17 may include two or more laser or television systems where each unit displays a different measured biological function or response. The SIM 17 may consist of a pattern of light produced by motor controlled beams of colored light beamed at the screen 51 where the speed of the resulting pattern is proportional to the subject's state of stress. Alternatively, the pattern of light may be produced by a back-lit liquid crystal screen, an oscilloscope screen, light emitting diode screen, or any other controlled method of producing a pattern of light. The SIM 17 may display more than one biological response by more than one method of producing a controlled pattern of light.

Figure 7:
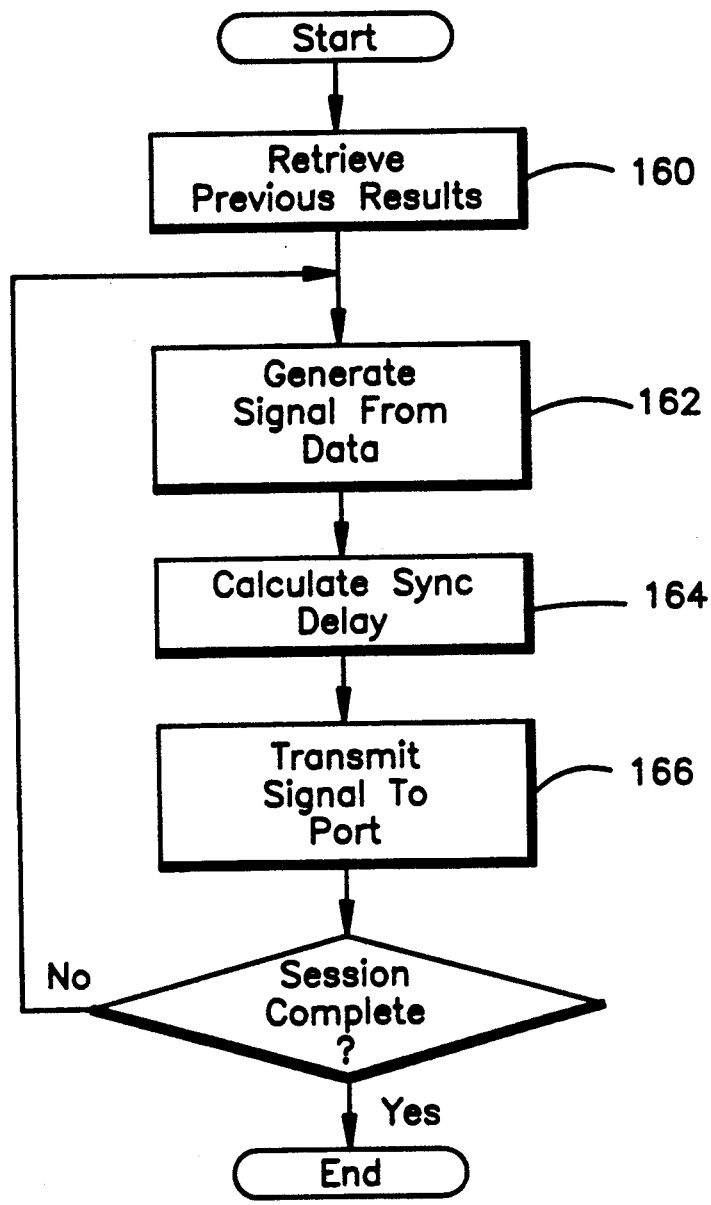
FIG. 7 is a flowchart showing the steps required to produce a target output used as an input to the apparatus of FIG. 6; and, FIG. 8 is a diagram showing a viewfield projection screen used in the system of the present invention.

FIG. 7 shows a flowchart for computer generation of the reference signal. In a previous session, a brief time slice, such as a few seconds, of the audio output signal produced by the computer program when the subject is fully relaxed will have been recorded on a mass storage device associated with the computer. The recording will take place in a way permitting at least approximate regeneration of the audio output signal from the stored data. For example, the signal may be sampled periodically and digital data representing the instantaneous voltage at the sampling points can be stored. In the subject's first session, a theoretical or average set of stored data can be used to generated the reference signal. This set of stored data typifies the subject's state at a lower stress level. Referring now to FIG. 7, the reference signal is generated by first retrieving the data representing previous results at block 160. The data is then placed in a sequential data stream to define a continuous signal, as shown at block 162. In the typical case, the signal being retrieved and generated will be sinusoidally based, so that the reference signal and the actual signal must be phase-aligned so that the subject may drive the actual stress signal and reference signal into approximate equality. Thus, in block 164, the actual stress signal is monitored and the phase timing of the generated reference signal may be compared to the actual stress signal to calculate a required delay to bring the two signals into coincidence. The resulting phase-matched output reference signal is then transmitted to an output port of interface card 24 at block 166 where it will be connected to leads 124 to control the steering mirror assembly 108, with the actual stress output signal controlling the steering mirror assembly 106. This process will be repeated until the end of the session, so that a continuous output reference signal is generated in phase with the actual stress output signal. In this way, reference data describing a brief time-slice of a signal can be used to produce a continuous, repeating reference signal pattern lasting for the duration of a session.

Figure 8:
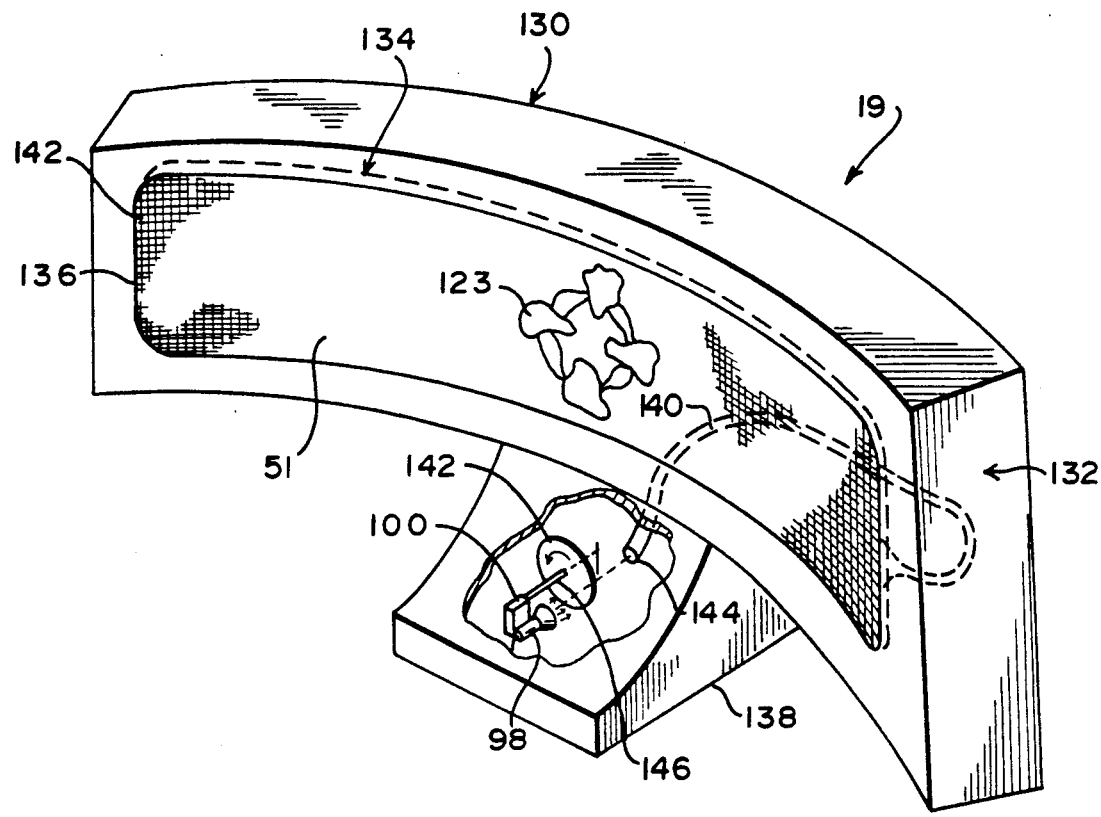

FIG. 8 shows the visual effects module 19 which serves to engage the visual attention of the subject by presenting to him a changing pattern of colored light. The pattern consists of abstract lines and/or geometric shapes. The pattern produces a soothing effect in the subject because the brain engages a major portion of its attention searching the changing light pattern for recognizable patterns while stress-producing thoughts are increasingly ignored. This effect is enhanced by adding to the complexity of the pattern up to the limit where the entire pattern is viewed by the brain as a single complex object. Complexity is increased by including greater numbers of "dimensions" to the pattern, including geometric patterns and movement in 1, 2, or 3 dimensions, changing shades of colors and changing shape and number of geometric objects. In order to achieve stress reduction, the overall emotional impact of the pattern must also be taken into account. For the purpose of stress reduction, cool colors such as blues, greens and violets should be used in repetitious complex patterns.

In the preferred embodiment, the visual effects module 19 consists of a projection unit 130 comprising a housing 132 with a semicircular screen 51 on its front surface. Screen 51 is constructed in accordance with the disclosures of one or more of U.S. Pat. Nos. 4,519,017 and 4,715,700 and application Ser. No. 07/105,829 filed Oct. 8, 1987. applications are incorporated herein by reference. In general, screen 51 is constructed in two layers: luminescent layer 134 and projection layer 136. The luminescent layer 134 is preferably made of a light-emitting material sold under the name Lumitex by Lumitex, Inc. of North Royalton, Ohio. The projection layer 136 is a layer of matte finish clear plastic. The screen 51 is generally rectangular in shape and measures about two feet in height and six feet in width. The screen 51 is placed at eye level with the subject and six to ten feet directly in front of the seated subject. The screen 51 is slightly curved to form a portion of a cylinder that "wraps around" the subject. The cylinder portion formed by screen 51 has a radius approximately equal to the distance from the subject's eyes to the screen surface and has its axis in the vertical direction. A base 138 provides support to position the screen 51 at the correct height, distance, and viewing angle to the seated or reclining subject. The housing 132 completely encases the screen 51, having a transparent window to expose the screen 51 to the viewer and being generally opaque on all other sides to both protect the screen 51 and associated mechanisms and to present a pleasing streamlined appearance to the subject. The base 138 and housing 132 comprise a stand-alone structure built to stand on the floor of the subject room 31 without requiring support by surrounding walls. The subject chair 55 is placed at a defined distance from projection unit 130 to ensure correct positioning of the subject relative to the screen 51. The screen 51 has sufficient reflective qualities that the Lissajous pattern 123 can be projected on it and viewed by the subject in the manner described previously.

The luminescent layer 134 is a woven fiber-optical fabric, having woven fibers forming at one end an optical fiber lightpipe cable 140. In operation, the high-intensity panel light 98 in base 138 beams light onto the end 144 of the lightpipe cable 140. Light enters lightpipe cable 140 and is trapped within the cable 140 by internal reflection until is reaches the other end of cable 140 where the individual fibers 140 of the luminescent layer 134 spread out and are woven into the luminescent layer 134. Small amounts of light trapped in the optical fibers 140 are emitted at each bend in the weave so that all the light is emitted by the time it reaches the end of the fibers 140. By adjusting the weave parameters a uniform emission of light can be achieved across the surface of the optical fiber fabric of luminescent layer 134.

A rotating colored wheel 142 is provided in the base 138 between panel light 98 and the end 144 of cable 140 and operates with the luminescent layer 134 as a means for providing colored patterns on the screen 51. A heat-resistant glass plate (not shown) may also be placed between panel light 98 and cable 140 to prevent melting of the cable 140 by heat emitted from panel light 98. In addition, a cooling fan (not shown) will normally be provided in the base 138 to exhaust and dissipate heat from panel light 98. Wheel 142 is constructed from heat-resistance glass such as Pyrex-brand glass and may be about 3½" in diameter. A large number of translucent color chips are attached to wheel 142 to form a plurality of colored regions. The color chips are constructed from color filter films or "gels" used in stage lighting and are attached to wheel 142 using epoxy. A coat of epoxy may also be provided over the color chips to seal them. Wheel 142 is rotated by wheel rotation motor 100 on a ¼" shaft 146. Relatively slow, precise rotation of the wheel 142 is desirable so that the patterns produced shift slowly and can be perceived by the subject. Therefore, the motor 100 will include suitable reducing gearing for producing a low rotational speed of shaft 146. As the wheel 142 rotates, the panel lamp 98 projects the color chips onto end 144 of cable 140. Colored stripes corresponding to the color chips will appear on the panel 134. By providing color chips of irregular shape and size, and by providing several chips of differing color along each radius of the wheel 142, the colored stripes will continually change in position, width, and color. The effects achieved include: geometric stripes in one dimension, geometric movement in one dimension, shades of color, changing colors, changing widths of geometric stripes, and changing numbers of geometric stripes.

The preferred embodiment of the visual effects module 19 provides abstract, complex visual effects of the type tending to distract the mind from stress-producing thoughts. It is a particular advantage of the design that this function is performed in combination with projection of stress state indication by stress state indicator module 17. The same screen, occupying the majority of the subject's field of view, is used for both relaxing image projection and stress state indication. This can be accomplished because the present invention provides the stress state indication in an abstract format which, while providing desired information on present stress levels relative to a target level, does not unduly distract the viewer from the relaxing images viewable on the same screen.

The preferred embodiment provides numerous advantages in terms of cost and effectiveness as compared to other visual systems. In particular, the cost of a similar-sized television screen capable of producing the same effects would be much higher. However, the method of display of the present invention, in which a Lissajous pattern created from multidimensional inputs is superimposed on an abstract relaxation image, might be accomplished using other technologies if desired. For example, the screen 51 might be replaced by television screens which display complex abstract images to the viewer as previously discussed or which may be used to display soothing natural images, such as waves rolling onto shore, or mountain streams and forests, clouds rolling across the sky, or the like as well as the Lissajous pattern. A kaleidoscope projector could also be used to present complex abstract images similar to those seen in these familiar children's toys. The visual effects module 19 might also be constructed using a matrix of small colored light bulbs which are turned on and off to form patterns of colored light. The visual effects module 19 may be a front or rear projection screen on which patterns are projected by means of a movie projector or by a slide projector. The visual effects module 19 may be a large mono-color or full-color liquid crystal "LC" screen which is programmed to display images or abstract patterns. The LC screen may be back-lit by conventional incandescent lamps, by fluorescent lamps, by a Lumitex screen, or by other means, or it may be front illuminated by conventional illuminating means. The visual effects module 19 may consist of an electroluminescent display, a plasma display, a diode display, or any one of dozens of other flat display devices. The visual effects module 19 could be a simple white screen 51 upon which a colored light pattern is projected by colored, focused or unfocused, lightbulbs placed around the rim of the screen 51. The screen 51 could be translucent and used with colored lamps placed behind the screen which turned on and off in various sequences to produce patterns of colored light.

A session begins when the operator uses the keyboard 41 to type in the subject's name and other information and instructs the SRS computer 23 to begin the session. The SRS computer 23 and software use timing information provided by a clock module in the SRS computer 23 to time the length of the session and to note the current date. The monitor 43 displays client billing information, previous session history, current session information and may possibly note the subject's preferences in control settings. Disk drives or other mass storage means in the SRS computer 23 may be connected to the SRS computer 23 to store the computer programs and client information.

The computer software is programmed to choreograph a relaxation session of a specific length in accordance with subject preferences in relaxing sound and taking into account the subject's state of stress as determined by the biological sensor information. A typical session will last for 30 minutes. At the beginning of the session, the stress state detection module 15, stress state indicator module 17, visual effects module 19, sound effects module 21, physical support and massage system 9, and environmental control module 13 will be activated. In general, these modules will remain activated during the entire session. As noted previously, the specific functions performed by the physical support and massage system 9 and environmental control module 13 may be varied as the session progresses, i.e. to massage and provide heat to successive different areas of the subject's body. In addition, the colored wheel 142 of the visual effects indicator module 19 may be controlled to rotate with a higher speed at the beginning of the session, and with a lower speed as the session progresses and the subject becomes more relaxed. In the computer controlled embodiment, the rotation of the colored wheel 142 may be controlled in response to the measured stress level of the subject so that the wheel 142 rotates more slowly as the subject becomes more relaxed. The SRS computer 23 is programmed to increasingly induce deeper states of relaxation as the session progresses and then to bring the subject back to the work-a-day environment near the end of the session through the selection of prerecorded sound tracks. The prerecorded sound tracks may consist of music, wave sounds, or other desired relaxing sounds, or a combination of sounds and music. The sound tracks used can be obtained commercially or may be specifically devised for the SRS 1. When the session is completed, the various subject modules 3 will be deactivated and the subject will emerge from the subject room 31.

We claim:

1. A stress reduction system comprising:
   stress detection means for sensing physiological indications of stress in a human subject and producting signals related to the subject's stress level;
   computing means connected to the stress detection means for receiving the stress level signals and processing the signals to determine the subject's stress level and product an output signal indicative of the present subject stress level;
   output indicating means connected to the computing means for providing a continuous visual indication of the present subject stress level to the subject using a visual display pattern having a visually perceived pattern complexity which at any given instant is related to the stress level;
   sensory stimulation means for selectively providing at least two diverse types of relaxing stimuli to the subject during an operational session of the system;
   control means comprising controlling circuits connected to the computing means and to the sensory stimulation means for selecting activating the computing and sensory stimulation means to orchestrate a relaxation session.

2. The system of claim 1 wherein said diverse types of relaxing stimuli produced by said sensory stimulation means comprise at least two of: audio, visual, tactile, temperature, vibrational, and olfactory stimuli.

3. The system of claim 2 further comprising support means associated with the sensory stimulation means for supporting the subject in a position to receive the relaxing stimuli thereof.

4. The system of claim 3 wherein the support means, the sensor stimulation means, and the output indicating means are located in an enclosure for isolating the subject, with the control means located outside the enclosure for activation by an operator.

5. The system of claim 4 wherein a plurality of subject enclosures are provided with a central control means controlling relaxation sessions in each of the subject enclosures.

6. The system of claim 2 wherein the control means selectively controls the sensory stimulation means in response to the subject's stress level.

7. The system of claim 2 wherein one of the sensory stimulation means includes a screen and projection means for displaying moving light patterns on the screen.

8. The system of claim 7 wherein the screen is constructed from woven fiber optic strands terminating in a cable having an input end.

9. The system of claim 8 wherein the projection means includes a source of varicolored light associated with the input end of the cable.

10. The system of claim 9 wherein the source of varicolored light includes a lamp and a moving, translucent color producing device interposed between the lamp and the input end of the cable, with the color producing device having a plurality of differently tinted zones for providing differently colored light at the input end of the cable.

11. The system of claim 7 wherein the output indicating means indicates the stress level to the subject using a light pattern with its complexity related to the stress level, with said light pattern projected on the screen.

12. The system of claim 7 wherein the sensory stimulation means further comprises means for producing sounds.

13. The system of claim 12 wherein the sensory stimulation means further comprises massage means associated with the support means for providing physical stimulation to the subject.

14. The system of claim 7 wherein the projection means projects star-type patterns on the screen.

15. The system of claim 7 wherein the projection means projects kaleidoscopic patterns on the screen.

16. The system of claim 1 wherein the complexity of the visual display pattern is greater for higher levels of stress and lower for lower levels of stress.

17. The system of claim 1 wherein the visual display pattern is generated using a laser beam.

18. A stress reduction system comprising:
    stress detection means for sensing physiological indications of stress in a human subject and producting signals related to the subject's stress level;
    computing means connected to the stress detection means for receiving the stress level signals and processing the signals to determine the subject's stress level and product an output signal indicative of the present subject stress level;
    output indicating means connected to the computing means for indicating the present subject stress level to the subject using a light pattern generated by a laser beam and having a complexity related to the stress level;
    sensory stimulation means for selectively providing at least two diverse types of relaxing stimuli to the subject during an operational session of the system, said stimuli comprising at least two of: audio, visual, tactile, temperature, vibrational, and olfactory stimuli;
    control means comprising controlling circuits connected to the computing means and to the sensory stimulation means for selecting activating the computing and sensory stimulation means to orchestrate a relaxation session;
    wherein the laser beam is deflected by at least one mirror moving in response to the output signal generated by the computing means to form a pattern.

19. The system of claim 18 wherein the laser beam is deflected in a first axis according to the output signal generated by the computing means and is deflected in a second axis according to a second signal generated by the computing means related to a target stress level to form a pattern including information on the relationship between the subject's stress level and a target stress level.

20. The system of claim 18 wherein the first and second axes are approximately perpendicular and the pattern is projected in a plane.

21. A method of reducing stress in a subject in a relaxation session using a stress reduction apparatus, comprising the steps of:
   a. locating the subject in a position appropriate to permit subject reception of relaxing stimuli from the stress reduction apparatus;
   b. detecting physiological indications of stress in a human subject and generating signals relating to the subject's stress level;
   c. providing a continuous visual indication to the subject of the present stress level using a viaual display pattern having a visually perceived pattern complexity which at any given instant is related to the stress level;
   d. providing sensory stimulation to the subject during the session using the stress reduction apparatus, said stimulation comprising at least two diverse stimuli from a class of stimuli including: audio, visual, tactile, temperature, vibrational, and olfactory stimuli.

22. The method of claim 21 wherein in step (a) subject is placed in a support means associated the stress reduction apparatus for supporting the subject in a position to receive relaxing stimuli.

23. The method of claim 21 wherein the visual display pattern is a laser light pattern.

24. The method of claim 23 wherein the laser light pattern is determined with reference to the subject's stress level and with further reference to a target stress level.

25. The method of claim 24 wherein the movement of the laser is controlled on a first axis by a signal related to the subject's stress level and on a second axis approximately perpendicular to the first axis by a signal related to the target stress level.

* * * * *